(12) United States Patent
Song

(10) Patent No.: US 9,039,898 B2
(45) Date of Patent: May 26, 2015

(54) METHOD FOR SEPARATING COMPONENTS IN NATURAL OIL

(75) Inventor: Yongsheng Song, Madison, AL (US)

(73) Assignee: Engineering Research Associates, Inc., Huntsville, AL (US)

( * ) Notice: Subject to any disclaimer, the term of this patent is extended or adjusted under 35 U.S.C. 154(b) by 702 days.

(21) Appl. No.: 13/297,115

(22) Filed: Nov. 15, 2011

(65) Prior Publication Data

US 2013/0121980 A1 May 16, 2013

(51) Int. Cl.
*B01D 11/04* (2006.01)
*B01D 17/02* (2006.01)
(Continued)

(52) U.S. Cl.
CPC .............. *A23D 9/02* (2013.01); *B01D 11/0284* (2013.01); *C11B 3/12* (2013.01); *C11B 1/10* (2013.01); *B01D 11/0492* (2013.01); *B01D 9/02* (2013.01);
(Continued)

(58) Field of Classification Search
CPC .... B01D 11/00; B01D 11/04; B01D 11/0492; B01D 17/00; B01D 17/02; B01D 17/0217; B01D 36/00; B01D 36/003; B01D 36/008; B01D 37/00; B01D 2251/50; B01D 2251/60; B01D 9/00; B01D 9/02; B01D 9/008; B01D 11/0284; B01D 11/028; B01D 3/00; B01D 3/009; C11B 3/00; C11B 3/006; C11B 7/00; C11B 7/0008; C11B 9/02; C11B 9/025; C11B 3/001; C11B 3/008; C11B 3/06; C11B 3/12; C11B 3/16; C11B 3/02; C11B 3/08; C11B 1/10; C11B 1/108; C11B 9/022
USPC ......... 210/634, 639, 774, 749, 752, 787, 806; 203/28, 29, 34–39; 159/47.1; 554/20, 554/174, 175, 206, 207, 208, 211; 426/417.425, 429, 601; 585/323, 351, 585/833, 864; 424/727; 549/413; 23/295 R, 23/296, 297, 298

See application file for complete search history.

(56) References Cited

U.S. PATENT DOCUMENTS 2,610,195 A * 9/1952 Gebhart ....................... 552/545
4,104,290 A 8/1978 Koslowsky
(Continued)

FOREIGN PATENT DOCUMENTS

EP 0671461 9/1995
JP 07-247495 9/1995

OTHER PUBLICATIONS

Publication: "Fractionation of palm oil": Current status, future possibilities", Ralph E. Timms, Paper presented at World Conference and Exhibition on Oilseeds and Vegetable Oil Utilization in Instanbul, Turkey, Aug. 14-16, 2006 and published in "Palm Oil, Jan. 2007, vol. 18, pp. 59-62.*

(Continued)

*Primary Examiner* — Joseph Drodge
(74) *Attorney, Agent, or Firm* — Jeremy A. Smith; Bradley Arant Boult Cummings LLP

(57) ABSTRACT

Different components of natural oils are separated by forming solid complexes of components of the natural oil with a solvent, and then separating the solid complexes from the remaining liquids. The natural oil is cooled in the presence of a solvent, and at least one component of the oil forms the solid complex with the solvent. This solid complex is separated from the remaining liquid portion of the oil solution, which also contains the solvent. Additional options concentration steps can further concentrate the components left in the liquid phase.

31 Claims, 8 Drawing Sheets

(51) Int. Cl.

| | |
|---|---|
| *B01D 9/02* | (2006.01) |
| *C11B 3/02* | (2006.01) |
| *C11B 3/12* | (2006.01) |
| *C11B 3/16* | (2006.01) |
| *A23D 9/02* | (2006.01) |
| *B01D 11/02* | (2006.01) |
| *C11B 1/10* | (2006.01) |
| *B01D 36/00* | (2006.01) |
| *C11B 3/00* | (2006.01) |

(52) U.S. Cl.
CPC .......... *B01D 17/0217* (2013.01); *B01D 36/003* (2013.01); *C11B 3/16* (2013.01); *C11B 3/001* (2013.01)

(56) References Cited

U.S. PATENT DOCUMENTS

| | | | |
|---|---|---|---|
| 4,486,353 A | | 12/1984 | Matsuzaki et al. |
| 4,880,658 A | | 11/1989 | Luddy |
| 5,157,132 A | * | 10/1992 | Tan et al. ................ 549/413 |
| 5,190,618 A | * | 3/1993 | Top et al. ................ 203/34 |
| 5,378,369 A | | 1/1995 | Rose et al. |
| 5,703,252 A | * | 12/1997 | Hunt et al. ................ 549/413 |
| 5,876,782 A | | 3/1999 | Sas et al. |
| 5,902,890 A | | 5/1999 | Nitsche et al. |
| 6,072,092 A | | 6/2000 | Ooi et al. |
| 6,207,187 B1 | | 3/2001 | Clark et al. |
| 6,350,453 B1 | | 2/2002 | Tan et al. |
| 6,358,997 B1 | | 3/2002 | Clark et al. |
| 6,395,915 B1 | | 5/2002 | Bellafiore et al. |
| 6,586,201 B1 | | 7/2003 | May et al. |
| 6,649,781 B2 | * | 11/2003 | Tou ................ 554/207 |
| 6,656,358 B2 | | 12/2003 | May et al. |
| 6,743,450 B2 | | 6/2004 | Romanczyk, Jr. et al. |
| 6,860,998 B1 | * | 3/2005 | Wilde ................ 210/634 |
| 6,867,308 B2 | | 3/2005 | Bartok et al. |
| 7,119,238 B2 | | 10/2006 | Khachik |
| 7,141,712 B2 | * | 11/2006 | Choo et al. ................ 585/864 |
| 7,161,055 B2 | | 1/2007 | Choo et al. |
| 7,507,847 B2 | * | 3/2009 | Tou ................ 554/206 |
| 7,544,822 B2 | * | 6/2009 | Ho ................ 554/175 |
| 2002/0025548 A1 | | 2/2002 | Sibeyn et al. |
| 2002/0082459 A1 | * | 6/2002 | Bailey et al. ................ 585/351 |
| 2003/0166951 A1 | * | 9/2003 | Blankenstein et al. ....... 549/529 |
| 2005/0250953 A1 | * | 11/2005 | May et al. ................ 549/413 |
| 2009/0312319 A1 | * | 12/2009 | Ren et al. ................ 514/234.2 |
| 2011/0220483 A1 | * | 9/2011 | Margnat et al. ................ 203/34 |

OTHER PUBLICATIONS

International Search Report and Written Opinion for International application No. PCT/US2011/061251.

* cited by examiner

METHOD FOR SEPARATING COMPONENTS IN NATURAL OIL

BACKGROUND OF THE INVENTION

1. Field of the Invention

This invention relates to methods for separating different components of a natural oil.

2. Background

Many natural oils are made up of several different components. These different components can include different types of oil compounds and many minor components. Some of the minor components are particularly valuable, including micro-nutrients and phytochemicals, and some people desire concentrated solutions of these valuable minor components. Some applications for different components include pharmaceutical uses, cosmetic uses, and even food preparation.

Crude palm oil can be used as one example of useful components in natural oils. Crude palm oil contains carotenoids, (pro-vitamin A), tocols (tocopherols and tocotrienols, which are forms of vitamin E), coenzyme Q10, squalene, phytosterols (sitosterol, stigmasterol, campesterol, and cholesterol), lecithin (phospholipids), and polyphenols. The benefits of these minor components are well documented. For example, carotenoids have been associated with the prevention of cardiovascular disease and macular degeneration, as well as the enhancement of the immune system. Tocols, and in particular tocotrienols, have been linked to neuro-protection and cardiovascular protection, as well as having anti-cancer effects such as anti-angiogenesis. Coenzyme Q10 has been linked to anti-cancer effects, and has been associated with cardiovascular benefits, enhanced cellular energy production, and antioxidative defense mechanisms. Research on squalene has suggested it inhibits cholesterol synthesis and thereby may promote cardiovascular health. Squalene has also been associated with anti-cancer effects including the suppression of skin and colon carcinogenesis. Similar studies have suggested anti-cancer and positive cardiovascular effects for phytosterols.

The separation and concentration of the different components of natural oil can damage some components of the oil. High heat, harsh chemicals, and other conditions which may be used to separate components can result in the degradation of certain compounds. The degradation of oil components not only reduces the amount of natural components present, but it also can produce unwanted degradation products. The health effects of these degradation by-products may not be favorable, and can even be harmful. Identification and testing of every degradation product is not practical, especially since the degradation products can change based on minor differences in feed stocks or process conditions, so the exact effect of degradation products can be variable and difficult to predict. Degradation products can also have other negative results, such as bad taste, dark color, or unpleasant smells.

Different chemicals can be used in the separation and concentration of different oil components, and traces or even high concentrations of these chemicals can remain in the separated components. Chemicals used to process natural oils should be safe for human contact, and even for human consumption, if the end products are intended for such uses. The different components of natural oil can be consumed by people, or come in contact with the skin, so the use of chemicals that are well understood and safe is preferred. Complete removal of a processing chemical can be difficult, expensive, and prone to unintended failures for certain out of specification batches. Use of a chemical that does not harm people minimizes the need for complete removal of the processing chemical, which often reduces processing costs because removal of trace quantities can be expensive. Use of a safe processing chemical also minimizes the ramifications if excesses of the processing chemical remain in the separated oil component.

The different components of natural oils are often valuable in a concentrated form, so the complete isolation of each individual component is not always required. Each separated component can still retain some quantity of the other components that were separated, and still remain valuable. Therefore, when the various components are separated, it does not necessarily mean the separation is a complete separation, but the separation should at least concentrate the specific component relative to the other components of the natural oil.

BRIEF SUMMARY OF THE INVENTION

Different components of natural oils are separated from each other for further use. The natural oil is cooled in the presence of a solvent, and one component of the oil forms a solid complex with the solvent. This solid complex is separated from the remaining liquid portion of the oil solution, which also contains the solvent. Several different techniques can be used to cool the oil in the presence of the solvent. There can also be additional concentration steps for the various separated oil components, such as removal of the solvent or further separation of different oil components.

DETAILED DESCRIPTION

Crude Palm Oil

Crude palm oil, also referred to as CPO, is one example of a natural oil. There are many other natural oils available, such as algae oil, corn oil, peanut oil, olive oil, soybean oil, rice oil, sesame oil, sunflower oil, and other vegetable oils, and each natural oil will typically have somewhat different characteristics and components. However, the basic principles described for CPO should also apply to other natural oils because the different natural oils all include triglyceride oil components, and these triglycerides should form solid complexes with certain solvents. The various components and processing chemicals may vary for different natural oils, but the general process is expected to work in a similar manner. The term "natural oil" is defined to mean an oil produced by a living organism, as opposed to petroleum oil that is produced over geologic time periods.

CPO contains at least a first component, a second component, and several minor components. In the CPO example, the first component is stearin oil, and the second component is olein oil. Both stearin and olein oil are present in the CPO as a triglyceride with relatively long fatty acid esters extending from a glycerol base. The minor components present in CPO may or may not be in the form of a triglyceride, and the minor components include micro-nutrients and phytochemicals. Many of the minor components contain an alcohol group, or an (OH) group, which tends to make the minor components at least somewhat more soluble in polar solvents than the stearin and olein oils.

Stearin oil has value on its own, as does olein oil, whether isolated from each other or combined. As a non-limiting example, olein oil can be used as cooking oil, and a combination of the stearin and olein oils may be used as feedstock for the food, detergent, or cosmetic industries. There are many uses for natural oils containing concentrated minor components from CPO, and these uses make the concentrated minor components valuable. The minor components of CPO can include carotenoids, tocols, coenzyme Q10, squalene, phytosterols, lecithin, and polyphenols. The exact components and concentrations in CPO can vary from batch to batch for many different reasons. The separated components of CPO, or other natural oils, can be further processed, blended, or reacted before it final use. These separated components may be sold with other chemicals present as well, such as solvents. Many of the uses for these separated components involve human consumption or skin contact, so the use of a solvent that is not hazardous is desirable.

Solid Complex Formation

Figure 1:
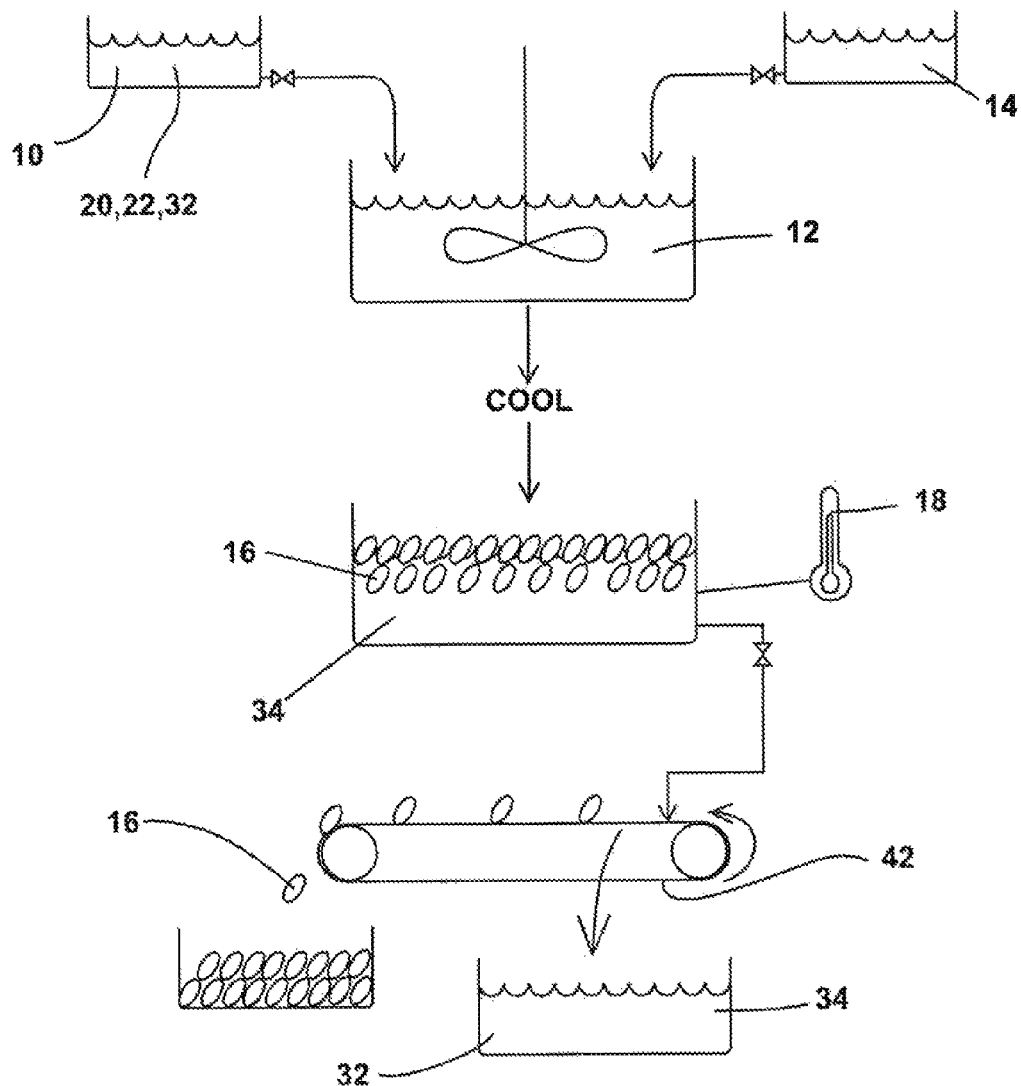
FIG. 1 is a schematic diagram of one embodiment of forming and separating a solid complex from natural oil.

Different components of natural oil 10 can be separated from each other by forming an oil solution 12 from natural oil 10 and a solvent 14, and then precipitating and separating solid complexes 16 from the oil solution 12, as seen in FIG. 1. In this description, the term "oil solution" 12 means a solution of a natural oil 10 and a solvent 14. In some cases, the natural oil 10 and solvent 14 may need to be heated for the natural oil 10 to dissolve or enter into solution with the solvent 14. The required temperature to produce the oil solution 12 depends on the relative concentration of the natural oil 10 and the solvent 14, amongst other factors, and oil solutions 12 can be obtained at lower temperatures with higher relative concentrations of the solvent 14, at least in certain circumstances.

It has been found that certain components of the natural oil 10 will form a solid complex 16 with certain solvents 14, and these solid complexes 16 can then be removed from the remaining liquid oil solution 12 by standard processes. The solid complexes 16 form at a solid complex formation temperature 18, and the solid complex formation temperature 18 may depend on process conditions, such as other chemicals which may be present, the solvent 14 and natural oil 10 used, pressure, etc. In lab trials, the solid complex formation temperature 18 can be a range of temperatures, where solid complexes 16 are formed beginning at one temperature and ending at a different temperature. This may be because many natural oils include several different components, and each different component may have a different solid complex formation temperature 18. It is also possible that other factors or reasons are responsible for the solid complex formation temperature 18 being a range instead of a fixed temperature.

Figure 2:
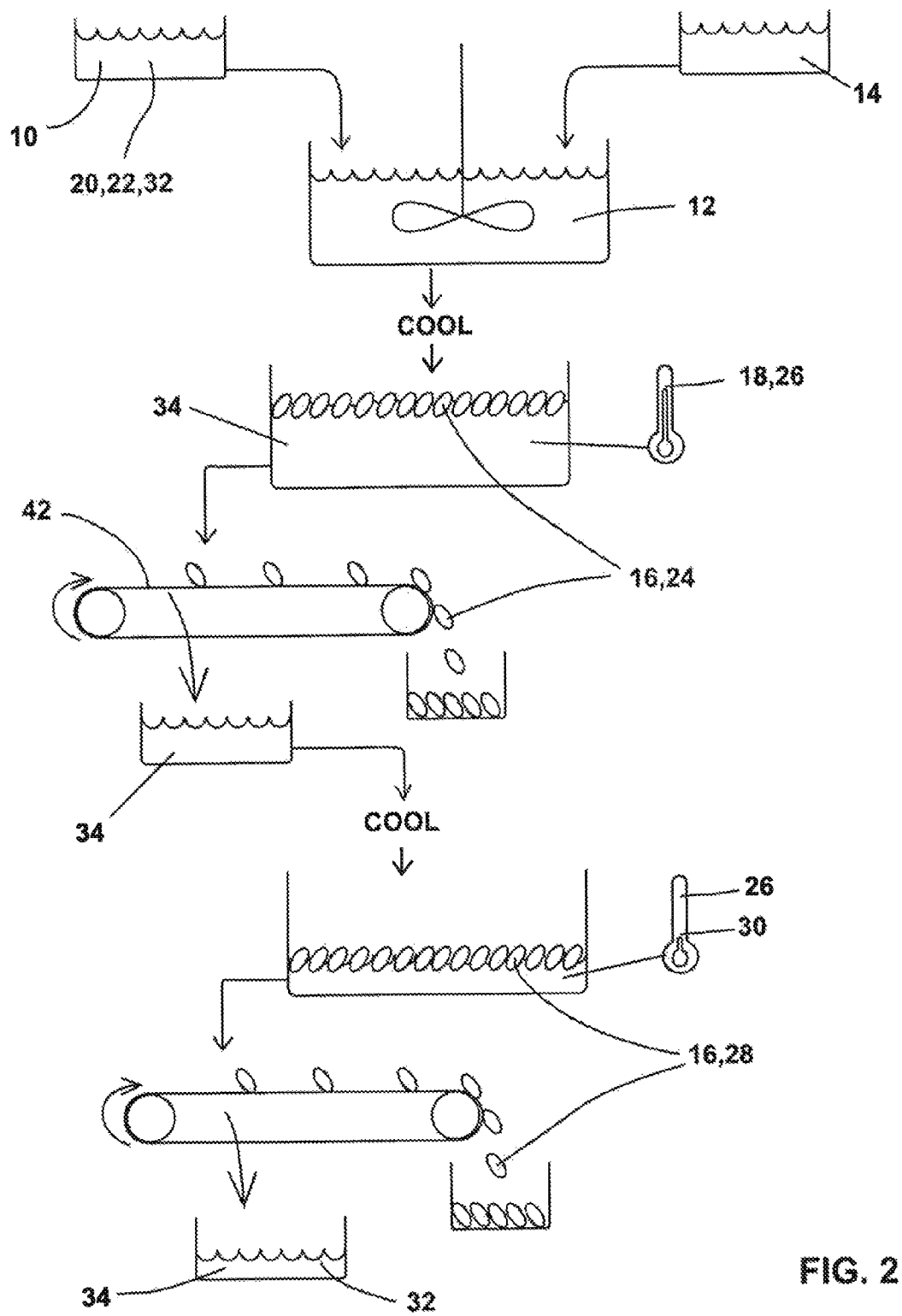
FIG. 2 is a schematic diagram of one embodiment of fractionally forming and separating solid complexes from natural oil.

The natural oil 10 is comprised of a first component 20 and a second component 22, and the first component 20 will form a first solid complex 24 with the solvent 14 at a first solid complex formation temperature 26, as seen in FIG. 2, with continuing reference to FIG. 1. The second component 22 will form a second solid complex 28 at a second solvent formation temperature 30, and the second solvent formation temperature 30 is lower than the first solvent formation temperature 26. In general, the first solid complex 24 will form as a solid when the temperature is below the first solid complex formation temperature 26, and the first solid complex 24 will liquefy, similar to a melting solid, when the temperature is above the first solid complex formation temperature 26. The behavior of the second solid complex 28 will correspond to that of the first solid complex 28, and the first and second solid complex formation temperatures 26, 30 will depend on the exact characteristics of the oil solution 12. The term solid complex 16 can include either one or both of the first and second solid complexes 24, 28, or more than the first and second solid complexes 24, 28. The natural oil 10 also comprises minor components 32, and the minor components may not form solid complexes 16 with the solvent 14, or the minor components 32 may only form solid complexes 16 with the solvent 14 at very low temperatures which are well below the first and second solid complex formation temperatures 26, 30.

The solid complexes 16 from CPO, and presumably of other natural oils 10, appear to be amorphous, as opposed to crystalline. In this description, a non-crystalline solid is defined to be "amorphous." Preliminary testing indicates the solid complexes 16 of CPO and ethanol are approximately 15-20% crystalline, which indicates the solid complexes 16 are primarily amorphous in nature (over 50% amorphous), and may even be at least 75% amorphous. Solid complexes 16 from other natural oils 10 and solvents 14 may well be primarily amorphous in nature as well. A solid complex 16 is a combination of different chemical compounds that are not covalently bonded together, so the different chemicals will readily separate when the solid complex dissociates. Many materials form crystals in the solid form, but oil molecules tend to be large and flexible. Therefore, solids formed with oils can be less likely to be crystalline than solids formed from many smaller atoms or molecules. Triglyceride natural oils 10 have three long "tails" that can bend and move essentially independent of each other, so these three "tails" of a triglyceride may hinder the formation of crystals. Testing and observation indicates the solid complexes 16 are primarily amorphous, and the reasons presented in this disclosure for the amorphous form are primarily conjecture.

The rate of sold complex formation has an effect on the purity of the material in the solid complex 16. In general, the slower a solid complex 16 forms, the better the chemicals are able to arrange themselves, and the purer the components of the solid complex 16 will be. When a solid complex 16 forms very rapidly, it can "trap" other materials in the matrix of the solid complex 16, and the rate of formation prevents the trapped materials from escaping the solid matrix. Therefore, a first solid complex 24 that was formed rapidly would probably contain more second components 22 and minor components 32 than a first solid complex 24 that was formed slowly. Of course, formation of the second solid complex 28 behaves similarly to that of the first solid complex 24.

Process for Separating Components in the Natural Oil

In general, the components of the natural oil 10 can be separated by cooling the natural oil 10 in a solvent 14 to form a solid complex 16, and then separating the solid complex 16 from the remaining liquids. This separates the natural oil components that form the solid complex 16 from the rest of the natural oil components, and thus serves to separate components in the natural oil 10. The separated solid complex 16 can be collected as a separate component of the natural oil 10. The minor components 32 tend to remain in the liquid, so the minor components 32 are concentrated in the liquid remaining in the oil solution 12 because removal of the solid complexes 16 removes a natural oil component. Therefore, the liquid remaining in the oil solution 12 after solid complexes 16 are separated is called the concentrated minor component oil 34, and the concentrated minor component oil 34 is one type of oil solution 12. It is possible to further concentrate the minor components 32 in the concentrated minor component oil 34, if desired. There are several different embodiments for separating components in the natural oil 10, as described below.

1. Fractional Solid Complex Formation

In some embodiments, the components of the natural oil 10 can be separated using fractional solid complex formation. In these embodiments, the oil solution 12 is cooled to a temperature lower than the first solid complex formation temperature 26, but higher than the second solid complex formation temperature 30, so the first solid complex 24 forms but the second solid complex 28 does not form. After the first solid complex 26 is formed, it is separated from the remaining liquid, and can be collected as a component of the natural oil 10. The liquid remaining after the first solid complex 26 is separated is the concentrated minor component oil 34 because some solid complex 26 has been removed, which concentrates the minor components 32. After the first solid complex 24 is separated, the remaining concentrated minor component oil 34 is further cooled to a temperature below the second solid complex formation temperature 30 so the second solid complex 28 forms. The second solid complex 28 can then be separated from the concentrated minor component oil 34, and the second solid complex 28 can be collected as a different component of the natural oil 10. The remaining concentrated minor component oil 34 can also be separately collected as another, different component of the natural oil 10.

The separately collected first and second solid complexes 24, 28 can then be individually heated to above the first and second solid complex formation temperatures 26, 30, respectively, so the solid complexes 16 dissociate into liquid oil and solvent layers. The solvent 14 can then be removed from the liquid first and second components 20, 22, if desired, and the first and second components 20, 22 can be separately processed, sold, or managed as desired.

2. Batch Cooling

In one embodiment, the "batch cooling" embodiment, natural oil 10 is combined with a solvent 14 to form an oil solution 12. The oil solution 12 is then batch cooled, where the term "batch cooled" means cooling a batch of oil solution 12 so the temperature of the oil solution 12 gradually lowers as the batch is cooled. A batch of oil solution 12 can be a partial component of a larger batch, but in batch cooling the natural oil 10 and solvent 14 in the oil solution 12 are cooled together, after the oil solution 12 is formed.

The oil solution 12 is cooled until a solid complex 16 is formed, and the solid complex 16 is separated from the remaining liquid in the oil solution 12. The solid complex 16 and the remaining concentrated minor component oil 34 can be separately collected as different components of the natural oil 10. This process can be expanded to include the fractional solid complex formation process described above.

The oil solution 12 can be cooled at a controlled rate, and a slower cooling rate can increase the purity of the solid complex 16 that is formed. This controlled cooling rate can also limit the minor components 32 that are incorporated into the solid complex 16, so the concentration of minor components 32 in the concentrated minor component oil 34 is also increased. In one embodiment, the oil solution 12 is cooled at a rate between 0.05 and 5 degrees centigrade per minute. In an alternate embodiment, the oil solution 12 is cooled at a rate between 0.1 and 2 degrees centigrade per minute. In yet another embodiment, the oil solution 12 is cooled at a rate of less than 0.05 degrees centigrade per minute. In still another embodiment, the oil solution is cooled at a rate of at least 1 degree centigrade per minute. The cooling rate can vary depending on the natural oil 10 and solvent 14 used, the amount of solvent 14 and natural oil 10 in the oil solution 12, the desired purity, any required process cycle time, and many other factors. The fractional solid complex formation process described above can be performed at controlled cooling rates, which can improve the purity of the separated first and second components 20, 22, as well as the remaining concentrated minor component oil 34. The controlled cooling rates reduce the quantity of minor components 32 entrained in the solid complexes 16, so there are more minor components 32 in the remaining concentrated minor component oil 34, and therefore the concentration of minor components 32 in the concentrated minor component oil 34 is increased by the gradual, controlled cooling rate.

3. Concentrated Oil Solution Cooling

Figure 3:
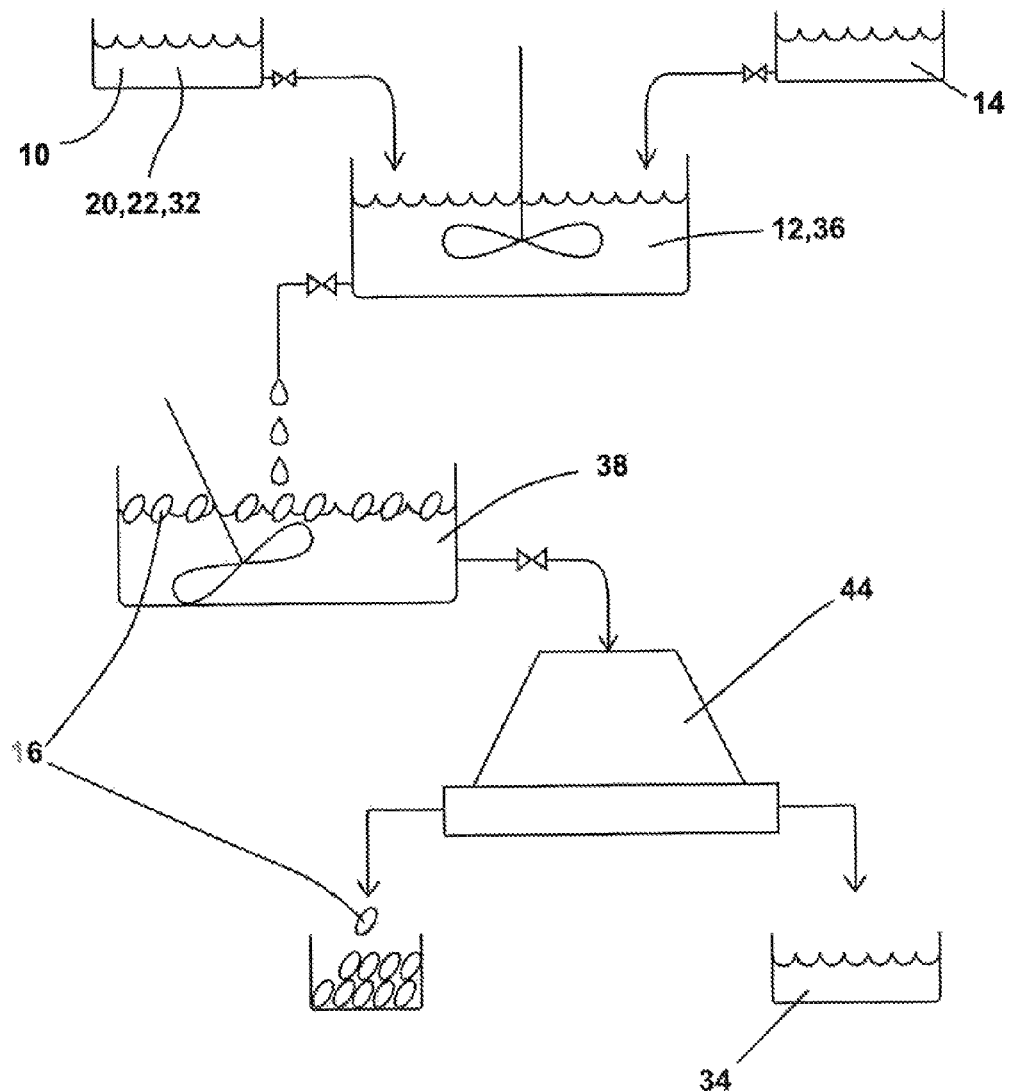
FIG. 3 is a schematic diagram of another embodiment of forming and separating a solid complex from natural oil.

In an alternate embodiment, the natural oil 10 is dissolved in a limited quantity of solvent 14 to form a concentrated oil solution 36, as seen in FIG. 3, with continuing reference to FIGS. 1 and 2. The concentrated oil solution 36 has a lower solvent concentration than the standard oil solution 12 described above. Because of the reduced solvent concentration, a higher temperature is usually required to dissolve the natural oil 10 in the limited quantity of solvent 14 in the concentrated oil solution 36 as compared to standard oil solution 12.

A cold solvent bath 38 is prepared separately from the concentrated oil solution 36, where the temperature of the cold solvent bath 38 is lower than the temperature required to dissolve the natural oil 10 in the concentrated oil solution 36. The temperature of the cold solvent bath 38 is also below the solid complex formation temperature 18. The contents of the concentrated oil solution 36 are then gradually added to the cold solvent bath 38, and solid complexes 16 are formed as the relatively hot concentrated oil solution 36 is rapidly cooled on immersion in the cold solvent bath 38.

The gradual addition of the concentrated oil solution 36 to the cold solvent bath 38 is generally comparable to a drop wise addition process that is frequently used in laboratory scale processes. The cold solvent bath 38 can be agitated during the addition of the concentrated oil solution 36 to disperse the solid complexes 16 and the remaining natural oil components. The cold solvent bath 38 can be controlled at a constant temperature during the addition of the concentrated oil solution 36, but it is also possible for the temperature of the cold solvent bath 38 to change during the concentrated oil solution 36 addition. The solid complexes 16 and the concentrated minor component oil 34 can then be separated and individually collected. After adding the concentrated oil solution 36 to the cold solvent bath 38, the cold solvent bath 38 can be further cooled to increase the amount of solid complexes 16 formed prior to separating the solid complexes 16 from the liquid. This embodiment can also utilize the fractional solid complex formation process described above by using more than one cold solvent bath 38, and dropping the collected liquid in a second cold solvent bath 38 to repeat the overall process.

The solid complexes 16 are formed very rapidly, because small amounts of the concentrated oil solution 36 are added to a relatively large amount of cold solvent. This rapidly cools the material in the concentrated oil solution 36, so the solid complexes 16 are rapidly formed. Therefore, the concentration of natural oil components in solution in the cold solvent bath 38 remains relatively low, because some of the natural oil components solidify almost immediately and are thus no longer dissolved in the cold solvent batch 38. Therefore, this embodiment can generally be used with a smaller total quantity of solvent 14 than the batch cooling process, because all the natural oil 10 is dissolved in the solvent 14 at the beginning of the batch cooling process. One potential advantage of this embodiment is reduced solvent usage. However, the solid complexes 16 are formed very rapidly in this embodiment, so this embodiment tends to produce lower purities than in the batch cooling process.

4. Hot Oil Cooling

Figure 4:
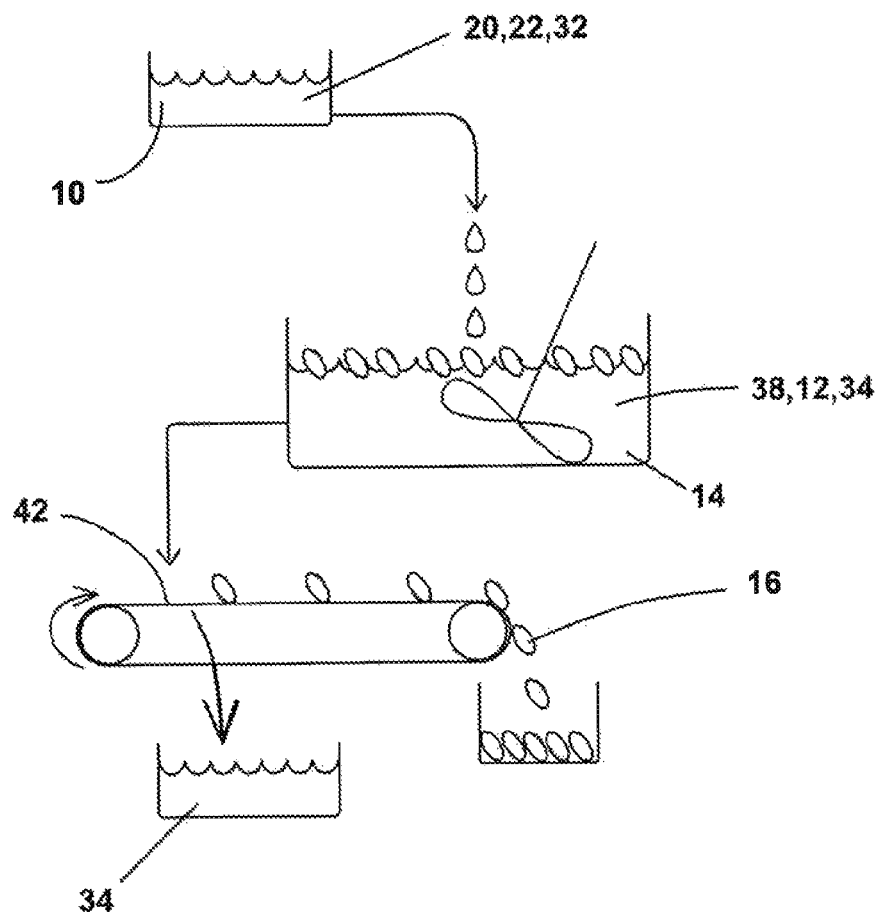
FIG. 4 is a schematic diagram of yet another embodiment of forming and separating a solid complex from natural oil.

In yet another embodiment, the natural oil 10 can be heated in an undiluted state to a point where it is liquid, as seen in FIG. 4, with continuing reference to FIGS. 1-3. This neat natural oil 10 liquid can then be gradually added to a cold solvent bath 38, similar to the concentrated oil solution cooling process described above. The solid complexes 16 form rapidly when each aliquot of neat natural oil 10 is added to the cold solvent bath 38, and the solid complexes 16 can be separated from the remaining concentrated minor component oil 34 and individually collected, as before. In this embodiment, the natural oil 10 is cooled in a solvent 14, because the cooling occurs when the natural oil 10 is added to the cold solvent bath 38. The fact that the natural oil 10 is not dissolved with solvent 14 prior to the cooling process does not change the fact that the natural oil 10 is cooled in the solvent 14.

This hot oil cooling embodiment has many similar characteristics with the concentrated oil solution cooling embodiment described above. The solid complexes 16 are formed rapidly, so the purity of the separated components is generally lower than the batch cooling process, but less solvent 14 can be used than in the batch cooling process. This hot oil cooling embodiment eliminates the step of preparing the concentrated oil solution 36 prior to cooling, so there is at least one less processing step. The fractional solid complex formation process can still be used, similar to the concentrated oil solution cooling embodiment, but the second cooling stage may start with an oil solution 12 instead of a neat natural oil 10, because the remaining natural oil 10 is dissolved in the solvent 14 of the cold solvent bath 38 during the formation of the first solid complexes 24. Alternatively, the solvent 14 can be separated from the remaining liquid concentrated minor component oil 34 after forming and separating the first solid complexes 24, so undiluted natural oil 10 could then be gradually added to another cold solvent bath 38 to form the second solid complex 28, if desired.

Solvent Properties

The process described herein depends on the formation of a solid complex 16 from a component of the natural oil 10 and the solvent 14. Therefore, the selection of the solvent 14 used in the process is important. The solvent selection parameters may vary somewhat with different natural oils 10, so the type of solvent 14 or the preferred solvent 14 which can be used may also vary. This description primarily describes the parameters for selecting solvent 14 to be used with CPO, so other solvent options may be investigated for other natural oils 10, but the general principles described here should apply to most natural oils 10.

In general, the selected solvent 14 should have an intermediate polarity. The solvent 14 should not be so polar that the natural oil 10 will not dissolve in it, but the solvent 14 should be polar enough for the natural oil 10 to partially dissolve in the solvent 14. It has been found that some solvents 14 of intermediate polarity form solid complexes 16 with components of the natural oil 10. If the solvent were non-polar, the natural oil 10 would likely remain in solution in the solvent 14 as the oil solution 12 cooled. In some embodiments, a solvent 14 with a dielectric constant between about 15 and 30, when measured at a temperature of 25 degrees centigrade, will form the solid complexes 16, but in other embodiments a solvent 14 with a dielectric constant between about 6 and 30 or even with a dielectric constant between about 5 and 50 will form the necessary solid complexes 16, where the dielectric constant is measured at a temperature of 25 degrees centigrade. In some embodiments, a protic solvent 14 can be preferential to an aprotic solvent 14.

The solvent 14 can be a mixture of different solvents 14, where the different solvents 14 can be mixed to provide the desired properties. For example, small quantities of water can be mixed with ethanol to increase the polarity of the resulting solution. Anhydrous ethanol tends to be more expensive that ethanol containing small quantities of water, so the ability to use ethanol with some water can lower costs. It has been found that water can be added to certain organic solvents 14 at a concentration of up to about 2% without interfering with the formation of solid complexes 16 in crude palm oil. Other mixtures of solvents 14 will likely be effective or even improve the effectiveness of the solvent 14 in forming solid complexes 16.

Many minor components 32 have an alcohol group, or an (OH) group, which tends to make these minor components 32 somewhat more soluble in polar solvents 14 than the triglyceride oil components. Therefore, the triglyceride oil components tend to form solid complexes 16 with the solvent 14 at a higher temperature than the minor components 32. This difference in polarity between the minor components 32 and the triglyceride oil components seems to aid in the selective formation of solid complexes 16 at varying temperatures, and also aids in the selection of a solvent 14. In general, it is preferable to select a solvent 14 that is more polar but still capable of forming an oil solution 12 with the natural oil 10.

When the natural oil 10 is crude palm oil (CPO), ethanol appears to be a good solvent 14. Other solvents 14 that do allow some separation of CPO include ethyl acetate and acetone, but ethanol provides better recovery. Methanol is more polar than ethanol, and methanol appears to be too polar for use with CPO, but methanol may be useful for other natural oils 10. Other aliphatic alcohols with 3 to 10 carbons may also allow separation of CPO, up to some maximum level of aliphatic carbons on the alcohol. Many other solvents 14 may also work with CPO or other natural oils 10, such as but not limited to water, acetonitrile, hexanes including cyclohexane), and tetrahydrofuran. Selecting a volatile solvent 14 can facilitate the later removal of that solvent 14 from the various natural oil components, because it is relatively easy to evaporate volatile solvents 14, and evaporation is a gentle separation technique. The solid complexes 16 of CPO components with ethanol were approximately ⅔ ethanol and ⅓ CPO components.

Additional Concentration of Minor Components

The minor components 32 in the concentrated minor component oil 34 can be further concentrated after the formation and separation of the solid complex 16, if desired. In some embodiments, the minor components 32 can be concentrated to 10 times their concentration in the original natural oil 10, but in other embodiments, at least some of the minor components 32 can be concentrated 100, 200, or even 250 times their original concentration.

The concentrated minor component oil 34 will often contain some triglyceride oil components, even after the formation and separation of solid complexes 16 described above. Removal of these remaining triglyceride oil components can further concentrate the remaining minor components 32 in the concentrated minor component oil 34.

Figure 5:
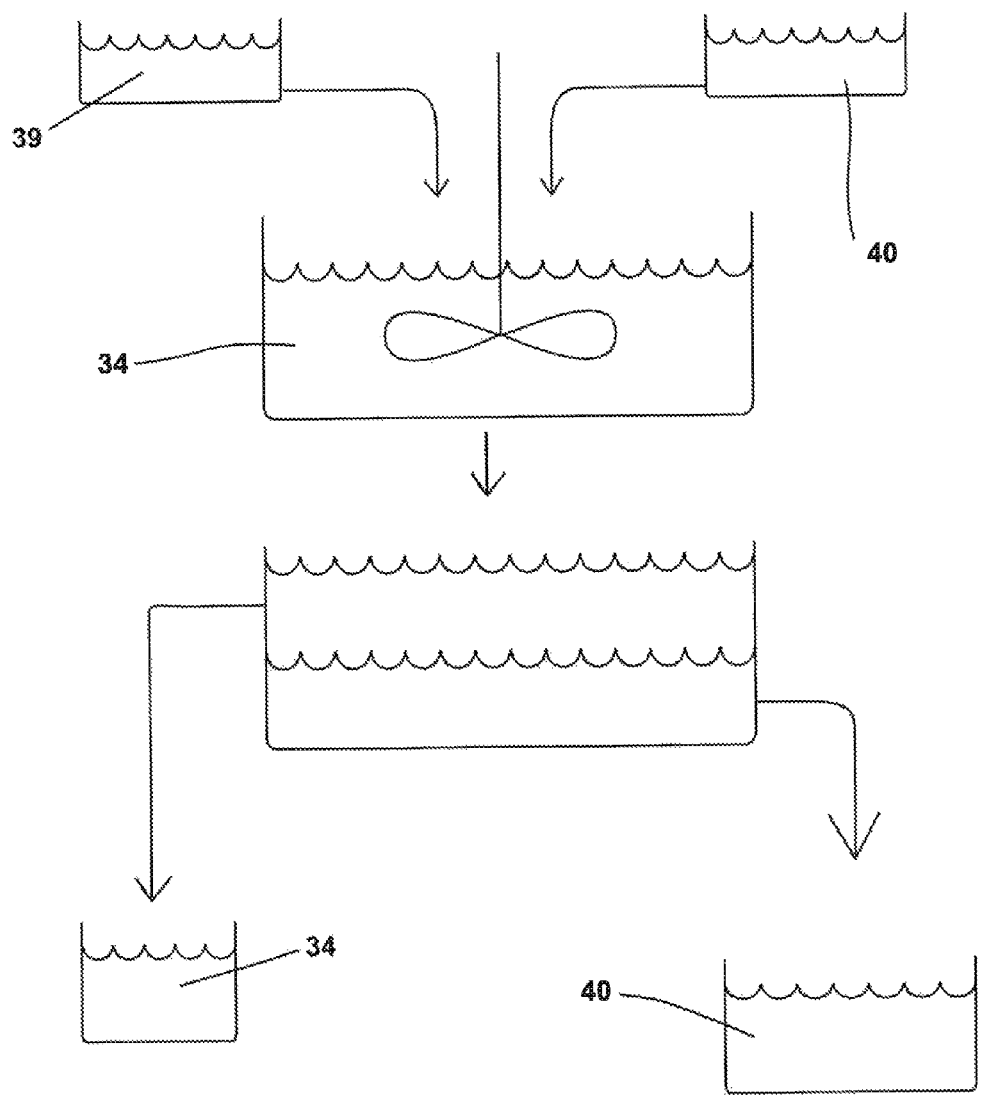
FIG. 5 is a schematic diagram of one embodiment of further concentrating the minor components of a natural oil after forming and separating a solid complex from the natural oil.

In one embodiment, a base 39 can be added to the concentrated minor component oil 34, which can break the bonds between the glycerol backbone and the remaining fatty acid portions of the oil components to form fatty acid metal salts, as seen in FIG. 5, with continuing reference to FIGS. 1-4. The base 39 can be sodium hydroxide, potassium hydroxide, sodium t-butoxide, potassium t-butoxide, or other bases 39, as desired. The metal salts can ionize and dissolve in water 40, but the remaining minor components 32 are not soluble in water 40. Therefore, water 40 can be added to form an aqueous layer and an oil layer. The water 40 can be added before the base 39, after the base 39, or at the same time as the base 39, as long as the base 39 can react with the triglyceride oil components.

The fatty acid metal salts will dissolve in the aqueous layer, and the remaining minor components 32 will remain in the oil layer. The oil layer can include the solvent 14 used to form the solid complexes 16, no solvent 14, or a different solvent 14 from the one used to form the solid complexes 16, as desirable for this processing step. The aqueous layer and the oil layer can then be split and separately collected, which further concentrates the minor components 32 in the remaining concentrated minor component oil 34. This step also separates the remaining triglyceride oil components in the natural oil 10, but these components are chemically altered before being separated. The remaining concentrated minor component oil 34 can then be washed with additional water 40 to remove any remaining base 39 or other water soluble compounds, if desired.

Figure 6:
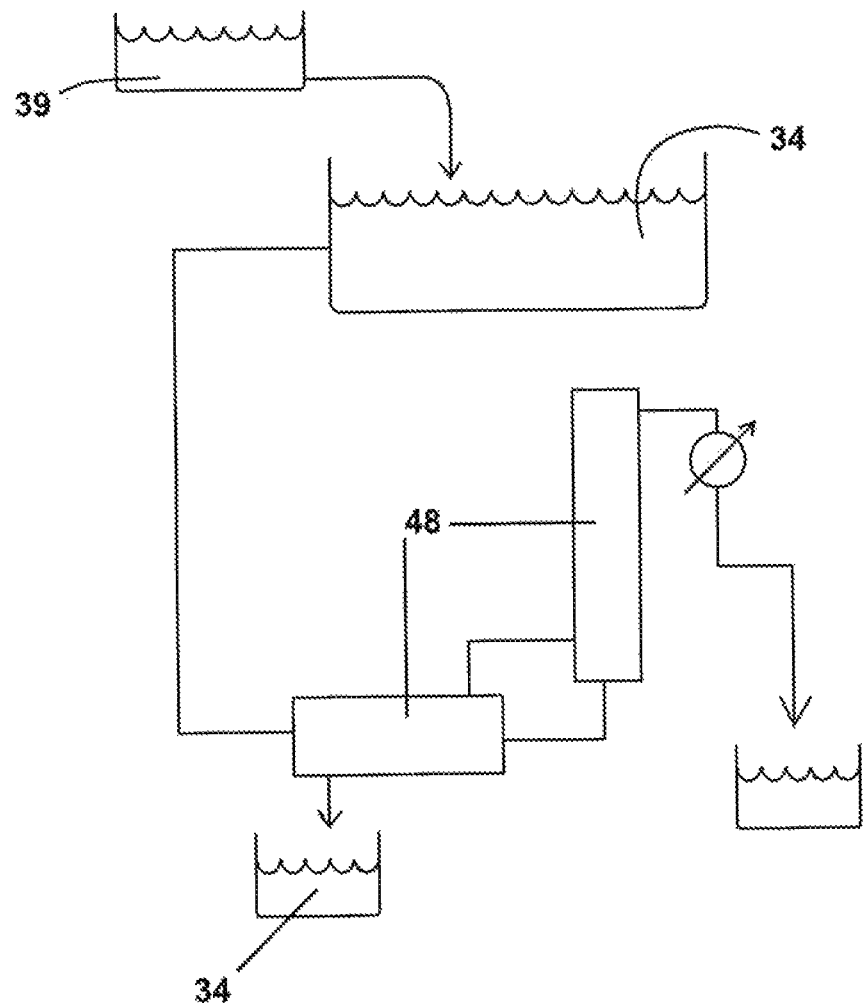
FIG. 6 is a schematic diagram of another embodiment of further concentrating the minor components of a natural oil after forming and separating a solid complex from the natural oil.

In an alternate embodiment, esterification of the remaining triglyceride oil components can be performed using known techniques, as seen in FIG. 6, with continuing reference to FIGS. 1-5. Esterification chemically separates the fatty acid components from the glycerol backbone, and forms esters from the fatty acids. This can involve a titration to determine the amount of base 39 catalyst to use, and the addition of the base 39 with an alcohol. If the solvent 14 is an alcohol, the alcohol for the esterification is already present. Esterification produces fatty acid esters, which is commonly referred to as biodiesel. The fatty acid esters can then be separated from the remaining minor components 32 by distillation or other techniques. The fatty acid esters are not soluble in water, so the water wash used with the fatty acid metal salts would not separate the fatty acid esters from the remaining minor components 32.

Each of these further concentration steps involves splitting the fatty acid elements from a triglyceride oil base. Other natural oil concentration processes based on splitting the fatty acid elements from a triglyceride oil base to allow separation of minor components 32 could also be used in combination with the formation and separation of solid complexes 16 from natural oils 10 described above.

The formation and separation of solid complexes 16 from natural oils 10, as described above, can be used as a first purification step, and a second purification step involving splitting the fatty acid elements from a triglyceride oil base can be used as a second purification step, as described above. The combination of these first and second purification steps can be more valuable than either step on its own. The first purification step is limited in the level to which the minor components 32 can be concentrated, and the second purification step produces a fatty acid based by-product. The first purification step removes most of the triglyceride oil based components from the natural oil 10 and provides a concentrated oil solution 36 to serve as the starting point for the second purification step. Therefore, most of the triglyceride oil based components in the natural oil 10 remain in the triglyceride oil form, as opposed to having the fatty acid components split from the triglyceride base, and these triglyceride oil based components can be processed and used in their natural form. Concentrating the minor components 32 before beginning the second purification step also improves the efficiency of the second purification step, because it reduces the amount of by-product fatty acid based material that must be separated from the remaining minor components 32. Therefore, combining the first purification step with the second purification step allows for the use of smaller equipment for the second purification step, the use of less raw materials in the second purification step, and improved recovery of minor components 32 in the second purification step because the collected minor components 32 are a greater percentage of the entire quantity of material processed. Therefore, the combination of one or more of the formation and separation of solid complexes 16 from natural oil steps described above (the first purification step) with one or more of the further purification steps involving splitting fatty acid components from triglyceride bases (the second purification step) can increase the value and effectiveness of each process on its own.

Solid Complex Separation

Figure 7:
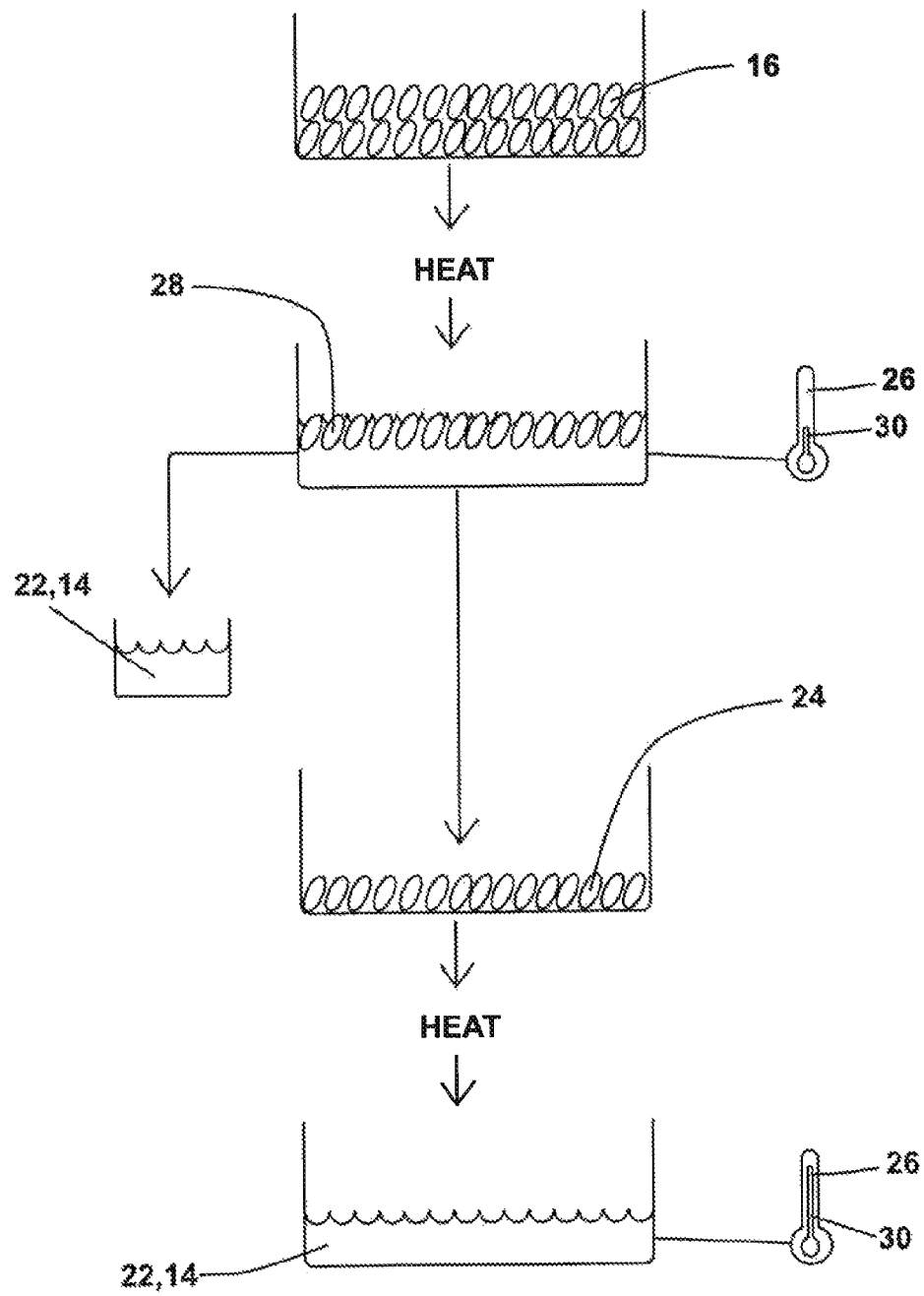
FIG. 7 is a schematic diagram of one embodiment of fractionally separating different solid complexes.
Figure 8:
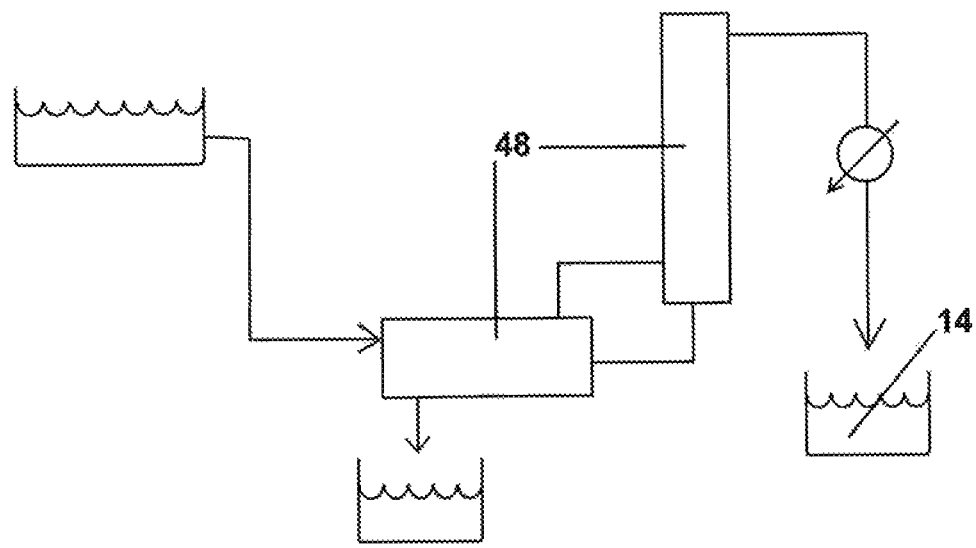
FIG. 8 is a schematic diagram of a distillation system to separate solvent from a solution.
Figure 9:
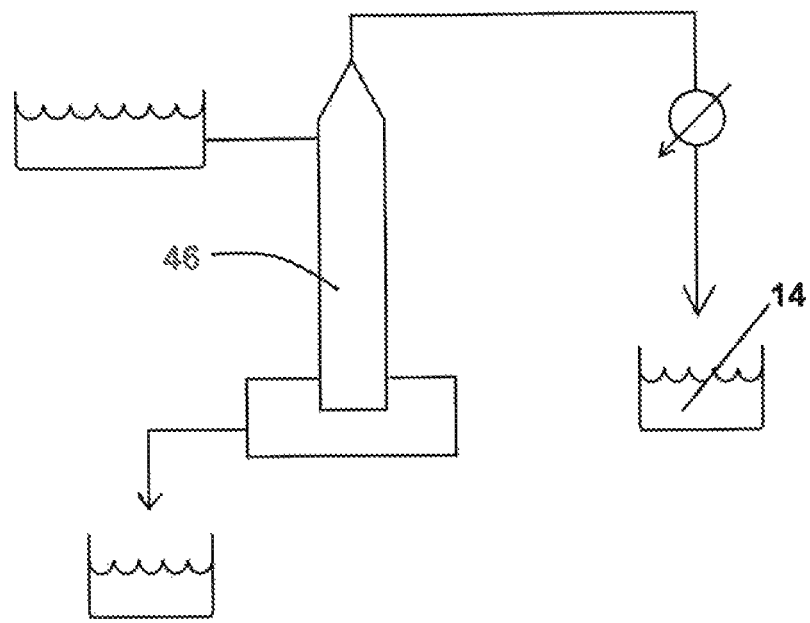
FIG. 9 is a schematic diagram of an evaporator to separate solvent from a solution.

Recovered solid complexes 16 can be separated after they are collected, if desired, as seen in FIG. 7, with continuing reference to FIGS. 1-6. The first and second solid complexes 24, 28 have different first and second solid complex formation temperatures 26, 30, respectively, where the first solid complex formation temperature 26 is higher than the second solid complex formation temperature 30. This difference in the first and second solid complex formation temperatures 26, 30 can be used to separate solid complexes 16 after collection.

Collected solid complexes 16 which contain both first and second solid complexes 24, 28 can be heated to a temperature between the first and second solid complex formation temperature 26, 30, so the second solid complex 28 will dissociate and form a liquid, but the first solid complex 24 will remain solid. At this point, the solid and liquid fractions can be separated and individually collected. The first and second components 20, 22 are separated at this point, with the first component 20 in a solid state and the second component 22 in a liquid state. The process can be carried further by heating the remaining first solid complexes 24 to a temperature above the first solid complex formation temperature 26, so the first solid complex 24 dissociates into a liquid. The liquid can be collected at this point. The solvent 14 can be separated from either one or each of the first and second components 20, 22, but the first and second components 20, 22 can also be further processed, sold or used with the solvents 14 present, as desired.

General Separation Techniques

Many different separation techniques can be used to perform the various separations discussed above, as seen in FIGS. 1-9. These separation techniques are discussed here because the same techniques can be used for several different steps described above. This separate discussion is intended to minimize unnecessary repetition.

Solid complexes 16 are separated from liquids in several different steps and embodiments. There are several different methods for separating solids from liquids. These include, but are not limited to: (i) filtration with filters 42, including Buchner funnels with filter membranes such as paper or cloth, filter belts, filter presses, bag filters, and many other types of filters 42; (ii) centrifugation with a centrifuge 44; and even (iii) skimming of the solids from the liquid. The techniques used to separate solids from liquids are not a critical component of this description, and the use of various techniques is envisioned.

Solvent 14 can be separated from the solid complexes 16 by dissociating the solid complex 16, and then evaporating the solvent 14. This can be done with an evaporator 46, open air evaporation, or other evaporating techniques. The solvent 14 can also be removed from the dissociated solid complex 16 by distillation in a distillation system 48, and may even be removed by water washes, resin absorption, or other techniques. Solvent 14 can be removed from the concentrated minor component oil 34 using the same techniques, except the concentrated minor component oil 34 generally does not need to be liquefied before solvent separation. Some of the separation processes described may also separate the solvent 14 from the natural oil components without dissociating the solid complex 16 beforehand. The techniques used to separate solvent from the natural oil components are not a critical component of this description, and the use of various techniques is envisioned.

Many of these separation techniques are very gentle, which helps to minimize degradation of the various natural oil components.

EXAMPLES

Several examples of various steps of the processes described above are presented in this Examples section. Tables with the relevant data are also presented. The examples use crude palm oil (CPO), but the process described should also separate the components of other natural oils 10. The concentrated minor component oil 34 is abbreviated as CMO in these examples.

Example 1

100.0 g of CPO is dissolved in 3 L (liters) of ethanol at around 60° C. (degrees centigrade). The solution is next cooled to around 40° C. at ambient temperature. The clear solution is then moved to a freezer with an internal temperature at −40° C. for further cooling for a period of 12 hours. After 12 hours, the temperature of the mixture is −40° C. In this step, oil molecules and organic solvent molecules form a small solid precipitate of oil-solvent solid complexes at low temperature while dissolving the minor components in the liquid CMO.

Next, to separate the solid complexes from the CMO, the solution is filtered with a Buchner funnel, and the solid complex is washed with cold ethanol (−40° C., 2×400 ml). The combined filtrates are evaporated at 70° C. to afford 8.0 grams of concentrated minor component oil (CMO) product. Detailed results from this step are shown in Table 1. The calculated recovery of total tocols shows experimental error, but is reproduced here to be complete.

Example 2

10.0 g of CPO is dissolved in 200 ml of acetone at 50° C. The clear orange solution is placed at ambient temperature for 1 hour, and then moved to a freezer at −40° C. for further cooling for a period of 10 hours. After 10 hours, the temperature of the solution is −40° C.

Next, the isolated oil solution is filtered with a Buchner funnel. The precipitate is washed with cold acetone (−40° C., 50 ml). The combined filtrates are evaporated at 60° C. to afford 0.8 grams of concentrated minor component oil (CMO). Detailed results from this step are shown in Table 2.

Example 3

100.0 g of CPO is dissolved in 300 ml of ethanol at 65° C. to form hot clear concentrated oil solution. Another 700 ml of ethanol is cooled to 10° C. as a cold solvent bath. The hot concentrated oil solution is added drop-wise into the cold solvent bath at a dropping rate of 25 ml/min and a stirring speed of 100 revolutions per minute (rpm). When the hot concentrated oil solution is dropped into the cold solvent bath, CPO oil forms small solids of CPO-ethanol solid complexes immediately. After complete addition of the hot concentrated oil solution into the cold solvent bath, the mixture is cooled in a freezer at −22° C. for approximately 10 hours until the temperature of the mixture is dropped down to −20° C.

The final mixture is filtered with a Buchner funnel. The solid precipitate is washed with cold ethanol (2×200 ml). The combined filtrates are evaporated and dried at 90° C. to afford 10 grams of concentrated minor component oil (CMO). Detailed results from this step are shown in Table 3.

The 333 g of solid precipitate of CPU-ethanol solid complexes are stable at up to 15° C. When heated to 30° C. or higher temperature, the solids dissociate and form two phases of CPO oil components and ethanol. Evaporation of the mixture of the two phases (total weight: 333 g) gives 90 g of pure CPO oil components and 243 g of ethanol.

Example 4

100.0 g of CPO is dissolved in 150 ml of isopropanol at 40° C. to form hot clear concentrated oil solution. Another 450 ml of isopropanol is cooled to 5° C. as a cold solvent bath. The hot concentrated oil solution is added drop-wise into the cold solvent bath at a dropping rate of 20 ml/min and a stirring speed of 200 rpm. After complete addition of the hot concentrated oil solution into the cold solvent bath, the mixture is cooled in a freezer at −20° C. for approximately 10 hours until the temperature of the mixtures is dropped down to −20° C.

The final mixture is filtered with a Buchner funnel. The filtrate is evaporated and dried at 90° C. to afford 8.8 grams of concentrated minor component oil (CMO) product. Detailed results from this step are shown in Table 4.

Example 5

100.0 g of CPO is heated to 60° C. to form hot clear natural oil (neat). The hot CPO is added drop-wise into an ethanol cold solvent bath at ambient temperature at a dropping rate of 120 ml/min and a stirring speed of 200 rpm. After addition of the hot natural oil, the mixture is cooled for approximately 10 hours until the temperature of the mixture is dropped down to −20° C.

The final mixture is filtered with a Buchner funnel. The solid precipitate is washed with cold ethyl alcohol (2×150 ml). The combined filtrates are evaporated and dried at 90° C. to afford 11.4 gram of concentrated minor component oil (CMO) product. Detailed results from this step are shown in Table 5.

Example 6

100.0 g of CPO is heated to 55° C. to form hot clear natural oil (neat). The hot CPO is added drop-wise into an ethanol cold solvent bath at ambient temperature (23° C.) at a dropping rate of 100 ml/min and a stirring speed of 280 rpm. After addition of the hot oil, the mixture is cooled in a water-bath to 16° C. in 20 minutes. Stearin precipitate commenced while cooling. The mixture is stirred at 16° C. for another 30 minutes and then filtered. The stearin precipitate (A) is washed with cold ethanol (10° C., 100 ml) and then dried at 80° C. under high vacuum to afford 55 g of stearin fat solid.

The combined filtrates are then continually cooled down to −20° C. in approximately 10 hours. The formed mixture is filtered and washed with cold ethanol (−20° C., 2×100 nl) to obtain olein precipitate (B) and combined concentrated minor component oil filtrate.

The precipitate (B) is evaporated and dried at 80° C. under high vacuum to afford 36 g of red olein oil (cooking oil). Detailed results from this step are shown in Table 6.

The combined filtrates are then evaporated and dried at 80° C. under high vacuum to yield 8.6 g of concentrated minor component oil (CMO) product. Detailed results from this step are shown in Table 7.

Example 7

100.0 g of CPO is dissolved in 150 ml of ethyl acetate with 2 of water at 40° C. to form hot clear concentrated oil solution. Another 350 ml of ethyl acetate with 2% of water is cooled to 5° C. as a cold solvent bath. The hot concentrated oil solution is added drop-wise into the cold solvent bath at a dropping rate of 20 ml/min and a stirring speed of 160 rpm. After complete addition of the hot concentrated oil solution into the cold solvent bath, the mixture is cooled in a freezer at −30° C. for approximately 10 hours until the temperature of the mixture is dropped down to −30° C.

The final mixture is filtered with a Buchner funnel. Both filtrate (A) and solid precipitate (B) are worked out as described below.

The solid precipitate (B) is washed with cold ethyl acetate (150 ml). The solid precipitate is kept in the Buchner funnel at ambient temperature for 2 hours, during which period the solid precipitate of oleins with ethyl acetate melts and passes through the filter, and the stearin solid stays in the filter. Both stearin solid and olein filtrate are evaporated and dried to yield 42 g of stearin solid and 45 g of red olein oil, respectively.

The filtrate (A) is evaporated and dried at 90° C. to yield 12.3 grams of concentrated minor component oil (CMO) product. Detailed results from this step are shown in Table 8.

Example 8

Saponification: concentrated minor component oil from the separation of solid complexes are further concentrated in accordance with one embodiment of the present disclosure. Minor component oil from each of the examples 1-7 listed above was combined together to form the minor component oil further processed in this Example 8. Namely, 49 grams (g) of concentrated minor component oil (CMO) is dissolved in 50 ml of ethanol at 40° C. under nitrogen. A degassed solution of sodium hydroxide (13 g) in water (150 ml) under nitrogen is next added to the solution. The mixture is then stirred at 40° C. under nitrogen for 10 hours. The reaction mixture with a pH of around 11 is then quenched by adding 70 ml of a saturated sodium bicarbonate solution to result in an ending pH between 9 and 10. The resulting mixture is next extracted with ethyl acetate (3×400 ml).

The aqueous phase is allowed to stand overnight and splits into a water phase and an oil phase. After separation of the oil phase from the water phase, the oil phase is washed with water and dried in an over at 120° C. to remove remaining water and solvent, and gives 51 g of free fatty acid sodium salts.

The combined ethyl acetate extracts are washed with saturated sodium carbonate (2×150 ml) and water (3×300 ml) respectively. The separated organic phase from the ethyl acetate extracts is next evaporated at 60° C. The resulting residue oil is then dried at 90° C. under high vacuum to afford 1.9 g of final minor component rich product. Detailed results from this step are shown in Table 9.

Example 9

Esterification: Minor component oil from each of the examples 1-7 listed above was combined together to form the minor component oil further processed in this Example 9. 9 g of the concentrated minor component oil is transferred to a degassed 20 ml solution of sodium methoxide in water at a concentration of 0.5 moles per liter (M) under nitrogen. The mixture is refluxed under nitrogen for 4 hours and then evaporated to remove methanol. The resulting residue is extracted with water and ethyl acetate. After separation of the two phases, the water phase is evaporated to give solid residue. It is washed with water and dried at 120° C. to give 5 g of free fatty acid sodium salts.

The organic phase is evaporated to afford 4.3 g of reddish oil. 4.0 g of the oil is distillated at 150° C. to afford 3.8 g of methyl esters (biodiesel) and 0.2 g of final minor component rich product. Detailed results from this step are shown in Table 10.

TABLES

Table 1, Example 1

TABLE 1

Carotenes and tocols recovered Example 1.

|  | CPO/ppm | CMO/ppm | Times increased | Recovery |
|---|---|---|---|---|
| Carotenes | 685 | 8250 | 12 | 96% |
| Total tocols | 1160 | 15882 | 13 | 109% |

Table 2, Example 2

TABLE 2

Carotenes and tocols recovered Example 2.

|  | CPO/ppm | CMO/ppm | Times increased | Recovery |
|---|---|---|---|---|
| Carotenes | 685 | 6992 | 10 | 82% |
| Total tocols | 1160 | 13908 | 12 | 96% |

Table 3, Example 3

TABLE 3

Carotenes and tocols recovered Example 3.

|  | CPO/ppm | CMO/ppm | Times increased | Recovery |
|---|---|---|---|---|
| Carotenes | 685 | 6165 | 9 | 90% |
| Total tocols | 1160 | 10788 | 9.3 | 93% |

Table 4, Example 4

TABLE 4

Carotenes and tocols recovered Example 4.

|  | CPO/ppm | CMO/ppm | Times increased | Recovery |
|---|---|---|---|---|
| Carotenes | 685 | 5238 | 7.6 | 67% |
| Total tocols | 1160 | 8225 | 7 | 62% |

Table 5, Example 5

TABLE 5

Carotenes and tocols recovered Example 5.

|  | CPO/ppm | CMO/ppm | Times increased | Recovery |
|---|---|---|---|---|
| Carotenes | 685 | 4911 | 7.2 | 82% |
| Total tocols | 1160 | 9668 | 8.3 | 95% |

Table 6, Example 6

TABLE 6

(Red olein oil): Carotenes and tocols recovered Example 6.

|  | CPO/ppm | Olein oil/ppm | Recovery |
|---|---|---|---|
| Carotenes | 685 | 400 | 21% |
| Total tocols | 1160 | 290 | 8% |

Table 7, Example 6

TABLE 7

(Concentrated minor component product): Carotenes and tocols recovered Example 6.

|  | CPO/ppm | CMO/ppm | Times increased | Recovery |
|---|---|---|---|---|
| Carotenes | 685 | 4866 | 7.1 | 61% |
| Total tocols | 1160 | 15701 | 10 | 86% |

Table 8, Example 7

TABLE 8

Carotenes and tocols recovered Example 7.

|  | CPO/ppm | CMO/ppm | Times increased | Recovery |
|---|---|---|---|---|
| Carotenes | 685 | 5144 | 7.5 | 92% |
| Total tocols | 1160 | 7506 | 6.5 | 79% |

Table 9, Example 8

TABLE 9

Results of final minor component product from saponification step

| Minor Components | Product after purification | Concentration in starting CPO |
|---|---|---|
| Carotene | 17.2% | 685 ppm |
| β-Carotene | 13.8% |  |
| α-Carotene | 3.4% |  |
| Lutein | 3.3% |  |
| Tocols | 24.2% | 1160 ppm |
| β-Tocotrienol | 3.0% |  |
| γ-Tocotrienol | 11.1% |  |
| α-Tocotrienol | 6.2% |  |
| α-tocopherol | 3.8% |  |
| α-tocomonoenol | 0.05% |  |
| α-tocopherolquinone | 0.05% |  |
| Squalene | 23.5% |  |
| Phytosterol | 9.3% |  |
| sitosterol | 5% |  |
| campesterol | 2% |  |
| sigmasterol | 2% |  |
| cholesterol | 0.3% |  |
| Co-enzyme Q10 | 0.55% |  |
| Free fatty acids and others | 21.95% |  |
| Total | 100% |  |

Table 10, Example 9

TABLE 10

Results of final minor component product from Esterification Step

| Minor Components | Product after purification | Concentration in starting CPO |
|---|---|---|
| Carotene | 9.4% | 685 ppm |
| β-Carotene | 7.4% |  |
| α-Carotene | 2% |  |
| Lutein | 3.2% |  |
| Tocols | 22.1% | 1160 ppm |
| β-Tocotrienol | 2.5% |  |

TABLE 10-continued

Results of final minor component product from Esterification Step

| Minor Components | Product after purification | Concentration in starting CPO |
|---|---|---|
| γ-Tocotrienol | 9.7% | |
| α-Tocotrienol | 6.6% | |
| α-tocopherol | 3.2% | |
| α-tocomonoenol | 0.05% | |
| α-tocopherolquinone | 0.05% | |
| Squalene | 15.3% | |
| Phytosterol | 8.3% | |
| sitosterol | 4% | |
| campesterol | 2% | |
| sigmasterol | 2% | |
| cholesterol | 0.3% | |
| Co-enzyme Q10 | 0.5% | |
| Free fatty acids and others | 41.2% | |
| Total | 100% | |

While the invention has been described with respect to a limited number of embodiments, those skilled in the art, having the benefit of this disclosure, will appreciate that other embodiments can be devised which do not depart from the scope of the invention as disclosed here.

The invention claimed is:

1. A method of concentrating minor components present in crude natural oil comprising:
   (a) combining the crude natural oil and a solvent and cooling the resulting mixture to below 0 degrees Centigrade at a first cooling rate of greater than 1 degree Centigrade per minute and a second cooling rate of less than 1 degree Centigrade per minute to form a primarily amorphous solid complex of the oil and solvent in a liquid oil solution; and
   (b) separating the solid complex from the liquid oil solution to form a concentrated minor component oil separate from the solid complex; and
   (c) performing a chemical extraction on the concentrated minor component oil, wherein said chemical extraction is selected from the group consisting of a saponification or an esterification reaction;
   wherein the concentrated minor component oil comprises at least (i) 22% tocols, (ii) 8% phytosterol, (iii) 7% b-carotene, (iv) 3% lutein, (v) 15% squalene, (vi) 0.5% co-enzyme Q10 and less than 50% free fatty acids by weight after a final drying step.

2. The method of claim 1 where step (a) further comprises: dissolving the crude natural oil in the solvent to form the oil solution; and batch cooling the oil solution.

3. The method of claim 1 where step (a) further comprises: dissolving the crude natural oil in a limited quantity of solvent to form a concentrated oil solution; preparing a cold solvent bath comprising the solvent; and adding the concentrated oil solution to the cold solvent bath at a gradual rate to produce the solid complex.

4. The method of claim 1 where step (a) further comprises: preparing a cold solvent bath comprising the solvent; and adding the crude natural oil in an undiluted state to the cold solvent bath at a gradual rate to form the solid complex.

5. The method of claim 1 further comprising:
   (c) further concentrating the minor components in the concentrated minor component oil after step (b).

6. The method of claim 5 where step (c) further comprises: adding a base to the concentrated minor component oil to form a fatty acid metal salt; adding water to the concentrated minor component oil to dissolve the fatty acid metal salts in a water phase; and splitting the water phase from an oil phase to further concentrate the minor components in the concentrated minor component oil.

7. The method of claim 5 where step (c) further comprises: esterification of the concentrated minor component oil to convert remaining natural oil triglycerides to separate fatty acid esters; and distillation of the concentrated minor component oil to separate the fatty acid esters from the minor components and thereby further concentrate the minor components in the concentrated minor component oil.

8. The method of claim 5 where step (c) further comprises evaporation of solvent from the concentrated minor component oil to further concentrate the minor components in the concentrated minor component oil.

9. The method of claim 1 where step (b) further comprises filtering the oil mixture to separate the solid complex from the liquid solution and form the liquid concentrated minor component oil.

10. The method of claim 1 wherein step (a) comprises cooling the crude natural oil and solvent solution to at least −20 degrees Centigrade.

11. The method of claim 10 wherein step (a) comprises cooling the crude natural oil and solvent solution to at least −40 degrees Centigrade.

12. The method of claim 1 where step (b) further comprises centrifuging the oil mixture to separate the solid complex from the liquid solution and forming the liquid concentrated minor component oil.

13. The method of claim 1 where the solvent has a dielectric constant at 25 degrees centigrade of between about 6 and 30.

14. The method of claim 1 where the solvent is selected from the group consisting of an organic alcohol containing 1 to 10 carbons, acetone, ethyl acetate, water, and any mixture thereof.

15. The method of claim 1 where the solvent comprises ethanol.

16. The method of claim 1 where the crude natural oil comprises crude palm oil.

17. The method of claim 1 where the minor components are concentrated by at least a factor of 10.

18. A method for separating different components from a crude natural oil comprising:
   (a) cooling crude natural oil in a solvent to at least −20 degrees Celsius at a rate of greater than 1 degree Centigrade per minute to form a primarily amorphous solid complex of the oil and solvent in a liquid oil solution, where the oil solution comprises the natural oil and the solvent;
   (b) separating the solid complex from the liquid oil solution; and
   (c) collecting the solid complex; and
   (d) performing a chemical extraction on the liquid oil solution, wherein said chemical extraction is selected from the group consisting of a saponification or an esterification reaction;
   wherein the liquid oil solution comprises at least (i) 7% b-carotene, (ii) 3% lutein, (iii) 15% squalene, (iv) 0.5% co-enzyme Q 10 and less than 50% free fatty acids by weight after a final drying step.

19. The method of claim 18 where the crude natural oil comprises a first component and a second component, where the first component foims a first solid complex with the solvent and the second component foams a second solid complex with the solvent, and where the method further comprises separating the first and second solid complexes from each other.

20. The method of claim 19 where steps (a) and (b) further comprises:
cooling the oil solution to below a first solid complex formation temperature to form a first solid complex; then
separating the first solid complex from the liquid oil solution; and then
cooling the oil solution to below a second solid complex formation temperature lower than the first solid complex formation temperature to form the second solid complex.

21. The method of claim 18 further comprising
(d) heating the collected solid complex to a temperature above a second solid complex formation temperature and below a first solid complex formation temperature after step (c), so the second solid complex becomes liquid; and
(e) separating the remaining solid complex from the liquids after step (d).

22. The method of claim 18 where the crude natural oil is crude palm oil comprising a first component and a second component, and where the first component comprises stearin oil and the second component comprises olein oil.

23. The method of claim 18 further comprising the step of separating the solvent from the solid complex.

24. The method of claim 18 where step (a) further comprises;
dissolving the natural oil in the solvent to form the oil solution; and
batch cooling the oil solution.

25. The method of claim 18 where step (a) further comprises:
dissolving the crude natural oil in a limited quantity of solvent to form a concentrated oil solution;
preparing a cold solvent bath comprising a solvent; and
adding the concentrated oil solution to the cold solvent bath at a gradual rate to produce the solid complex.

26. The method of claim 18 where step (a) further comprises:
preparing a cold solvent bath comprising a solvent; and
adding the natural oil in an undiluted state to the cold solvent bath at a gradual rate to form the solid complex.

27. The method of claim 18 where step (b) further comprises filtering the oil solution to separate the solid complex from the liquid oil solution.

28. The method of claim 18 where step (b) further comprises centrifuging the oil solution to separate the solid complex from the liquid oil solution.

29. The method of claim 18 where the solvent has a dielectric constant between about 15 and 30.

30. The method of claim 18 where the solvent comprises a protic solvent.

31. The method of claim 18 where the solvent comprises ethanol.

* * * * *